United States Patent
Owens et al.

(10) Patent No.: US 9,788,583 B1
(45) Date of Patent: Oct. 17, 2017

(54) MEDICAL TUBE SAFETY DEVICE

(71) Applicant: Innovations Unlimited, LLC, Pennsauken, NJ (US)

(72) Inventors: Dorothy M. Owens, Erial, NJ (US); Darleen M. Sawyer, Pennsauken, NJ (US)

(73) Assignee: Innovations Unlimited, LLC, Pennsauken, NJ (US)

( * ) Notice: Subject to any disclaimer, the term of this patent is extended or adjusted under 35 U.S.C. 154(b) by 0 days.

(21) Appl. No.: 15/606,654

(22) Filed: May 26, 2017

Related U.S. Application Data (60) Provisional application No. 62/493,070, filed on Jun. 20, 2016.

(51) Int. Cl.
- *A61M 16/04* (2006.01)
- *A41D 13/12* (2006.01)
- *A61M 5/14* (2006.01)
- *A61M 16/08* (2006.01)
- *A61M 39/10* (2006.01)

(52) U.S. Cl.
CPC ..... *A41D 13/1281* (2013.01); *A41D 13/1245* (2013.01); *A61M 16/0497* (2013.01); *A61M 5/1415* (2013.01); *A61M 16/0465* (2013.01); *A61M 16/08* (2013.01); *A61M 39/1011* (2013.01); *A61M 2005/1416* (2013.01); *A61M 2205/15* (2013.01); *A61M 2205/18* (2013.01)

(58) Field of Classification Search
CPC .......... A61M 16/0497; A61M 16/0465; A61M 2025/0266; A61M 2025/0206; A61M 16/04
See application file for complete search history.

(56) References Cited

U.S. PATENT DOCUMENTS

| | | |
|---|---|---|
| 3,595,228 A | 7/1971 | Heron et al. |
| 4,259,965 A | 4/1981 | Fukuda et al. |
| 5,578,003 A | 11/1996 | Borger |
| (Continued) | | |

FOREIGN PATENT DOCUMENTS

| | | |
|---|---|---|
| CN | 203355067 U | 12/2012 |
| JP | 20050232806 | 8/2005 |
| WO | WO 2014-078751 A1 | 5/2014 |

OTHER PUBLICATIONS

Conrad, David, "Tracheostomy Alarm for Accidental Decannulation", UCSF Innovation, Technology & Alliances, Tech ID 27136 / UC Case 2016-206-1, 2016, 1 page.

*Primary Examiner* — Hongmin Fan
(74) *Attorney, Agent, or Firm* — Baker & Hostetler LLP (57) ABSTRACT

The invention includes an alarm assembly configured to engage a tube that is capable of extending into a patient. The alarm assembly comprises alarm circuitry, a wound dressing configured to releasably attach to the patient that includes at least one actuator, and a sensor holder. The sensor holder is configured to be releasably coupled to the tube and includes at least one sensor. The at least one sensor is configured to transmit a signal to the alarm circuitry when the at least one actuator actuates the at least one sensor, and the alarm circuitry is configured to produce an alert in response to receiving the signal. The invention also includes a method of detecting a tube dislodging from a patient, as well as a kit comprising a tube, alarm circuitry, a wound dressing, and a sensor holder.

20 Claims, 9 Drawing Sheets

(56) References Cited

U.S. PATENT DOCUMENTS

| | | | |
|---|---|---|---|
| 6,105,577 A * | 8/2000 | Varner | A61M 16/0465 |
| | | | 128/207.14 |
| 6,588,426 B2 | 7/2003 | Linderoth | |
| 7,416,532 B1 | 8/2008 | Broshears | |
| 7,874,999 B2 | 1/2011 | Busby | |
| 2013/0213405 A1* | 8/2013 | Dillworth | A61M 16/0497 |
| | | | 128/207.17 |
| 2013/0255691 A1 | 10/2013 | Mansfield et al. | |
| 2015/0283351 A1 | 10/2015 | Castello et al. | |
| 2015/0297866 A1 | 10/2015 | Hyman et al. | |
| 2016/0114142 A1 | 4/2016 | Ziaie et al. | |
| 2016/0250466 A1 | 9/2016 | Boggs, II et al. | |

* cited by examiner

MEDICAL TUBE SAFETY DEVICE

CROSS REFERENCE TO RELATED APPLICATIONS

The present application claims priority to and the benefit of U.S. Provisional Application Ser. No. 62/493,070, filed Jun. 20, 2016, the entire disclosure of which is incorporated by reference into this application.

TECHNICAL FIELD

This disclosure generally relates to alarm assemblies that are used to detect movement of a tube that is capable of delivering material to the interior of a human, and subsequently alert medical personnel and caregivers of the detected movement.

BACKGROUND

During or after medical procedures, tubes may need to be inserted into a patient to deliver materials, such as fluids or gasses, to the patient. For example, tracheotomies can be performed on patients who suffer from facial trauma or tumors of the head and/or neck. Tracheotomies involve creating an incision in the trachea, which can serve as the entryway for the insertion of a tracheal tube. Tracheal tubes allow a patient to breathe without using the patient's nose or mouth.

However, over time, a tube, such as a tracheal tube, can become dislodged from the patient to the point that the patient no longer receives the material supplied by the tube. In the case of a tracheotomy, sufficient dislodgment of the tracheal tube can prevent the patient from receiving adequate oxygen, which can lead to serious injury or death. As such, there is a need for a device that notifies the patient, medical professional, or other caregiver that the tube has been dislodged, so that the patient or caregiver can take quick and effective corrective action to return the tube to a normal working configuration.

SUMMARY

An embodiment of the present disclosure includes an alarm assembly that is configured to engage a tube that is capable of extending into a patient, where the tube defines a main body. The alarm assembly comprises alarm circuitry and a wound dressing that is configured to releasably attach to the patient. The wound dressing includes at least one actuator. The alarm assembly also includes a sensor holder that is configured to be releasably coupled to the tube. The sensor holder including at least one sensor, and the at least one actuator is configured to actuate the at least one sensor when the at least one sensor moves from a first position to a second position. The second position is further from the at least one actuator than the first position. Additionally, the at least one sensor is configured to transmit a signal to the alarm circuitry when the at least one actuator actuates the at least one sensor, and the alarm circuitry is configured to produce an alert in response to receiving the signal.

Another embodiment of the present disclosure includes a method of detecting a tube dislodging from a patient. The method includes the step of attaching a wound dressing to the patient, where the wound dressing includes at least one actuator. The method also includes the step of attaching a sensor holder to the tube, where the sensor holder includes at least one sensor. The at least one actuator is configured to actuate the at least one sensor when the at least one sensor moves from a first position to a second position, where the second position is further from the at least one actuator than the first position. The method further includes the step of transmitting a signal from the at least one sensor to an alarm circuitry when the at least one actuator actuates the at least one sensor. Additionally, the method includes the step of producing an alert via the alarm circuitry when the alarm circuitry receives the signal.

Another embodiment of the present disclosure includes a kit that comprises a tube defining a main body, where the tube is capable of extending into a patient. The kit also includes alarm circuitry, and a wound dressing configured to releasably attach to the patient. The wound dressing includes at least one actuator. The kit further includes a sensor holder configured to be releasably coupled to the tube, where the sensor holder includes at least one sensor. The at least one actuator is configured to actuate the at least one sensor when the at least one sensor moves from a first position to a second position, where the second position is further from the at least one actuator than the first position. The at least one sensor is configured to transmit a signal to the alarm circuitry when the at least one actuator actuates the at least one sensor, and the alarm circuitry is configured to produce an alert in response to receiving the signal.

BRIEF DESCRIPTION OF THE DRAWINGS

The foregoing summary, as well as the following detailed description, will be better understood when read in conjunction with the appended drawings. The drawings show illustrative embodiments of the disclosure. It should be understood, however, that the application is not limited to the precise arrangements and instrumentalities shown.

DETAILED DESCRIPTION OF ILLUSTRATIVE EMBODIMENTS

Described herein are multiple embodiments of an alarm assembly that is configured to engage a tube that is capable of extending into a patient. Certain terminology is used to describe the alarm assembly in the following description for convenience only and is not limiting. The words "right", "left", "lower," and "upper" designate directions in the drawings to which reference is made. The words "inner" and "outer" refer to directions toward and away from, respectively, the geometric center of the description to describe the alarm assembly and related parts thereof. The terminology includes the above-listed words, derivatives thereof and words of similar import.

Unless otherwise specified herein, the terms "longitudinal," "transverse," and "lateral" are used to describe the orthogonal directional components of various components of the alarm assembly, as designated by the longitudinal direction 12, lateral direction 13, and transverse direction 14. It should be appreciated that while the longitudinal and lateral directions 12 and 13 are illustrated as extending along a horizontal plane, and the transverse direction is illustrated as extending along a vertical plane, the planes that encompass the various directions can differ during use.

Figure 1A:
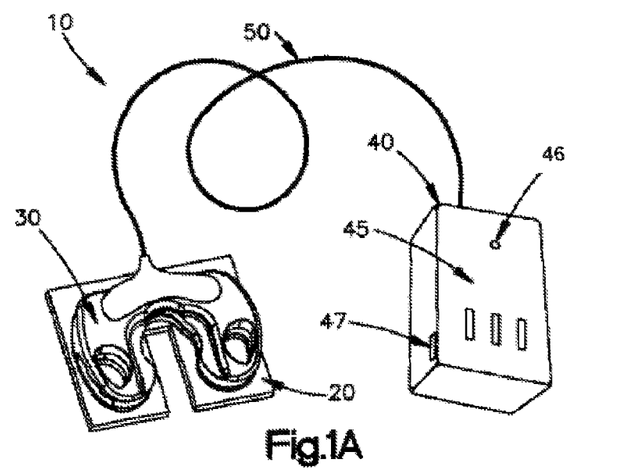
FIG. 1A is top view of a fully assembled alarm assembly according to an embodiment of the present disclosure.
Figure 1B:
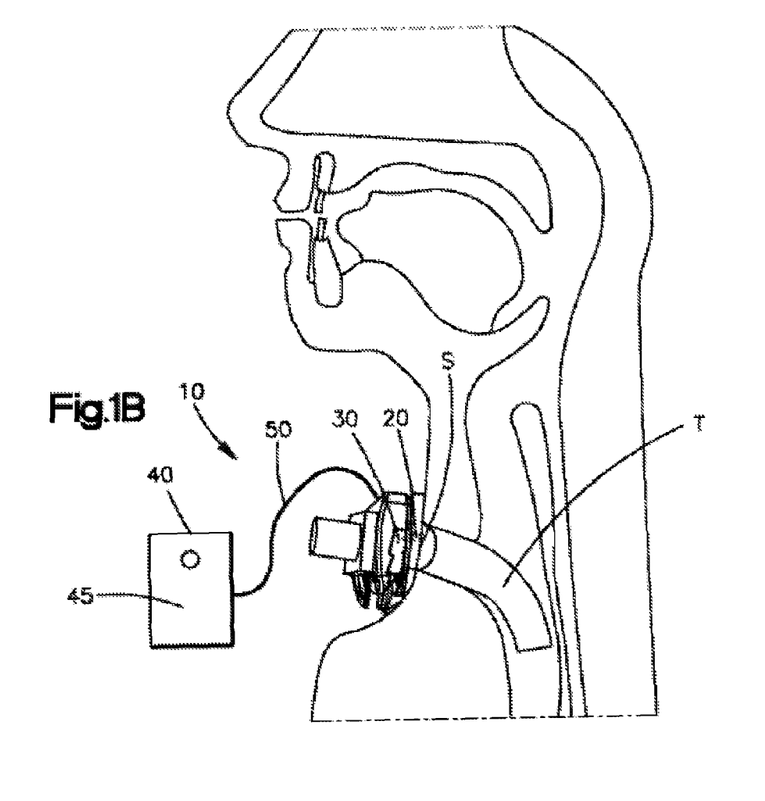
FIG. 1B is a view of the fully assembled alarm assembly illustrated in FIG. 1A attached to a patient.
Figure 10A:
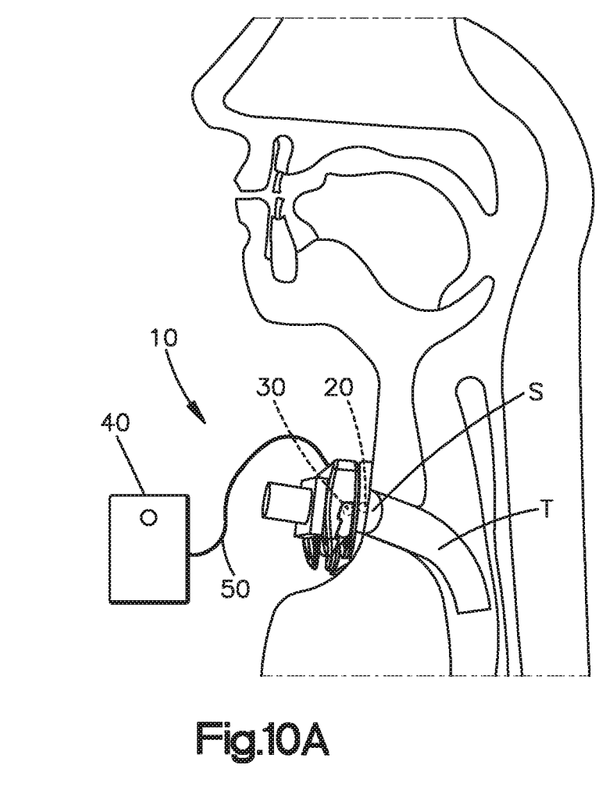
FIG. 10A is a view of a fully assembled alarm assembly of an embodiment of the present disclosure, where the alarm circuitry is not producing an alert.
Figure 10B:
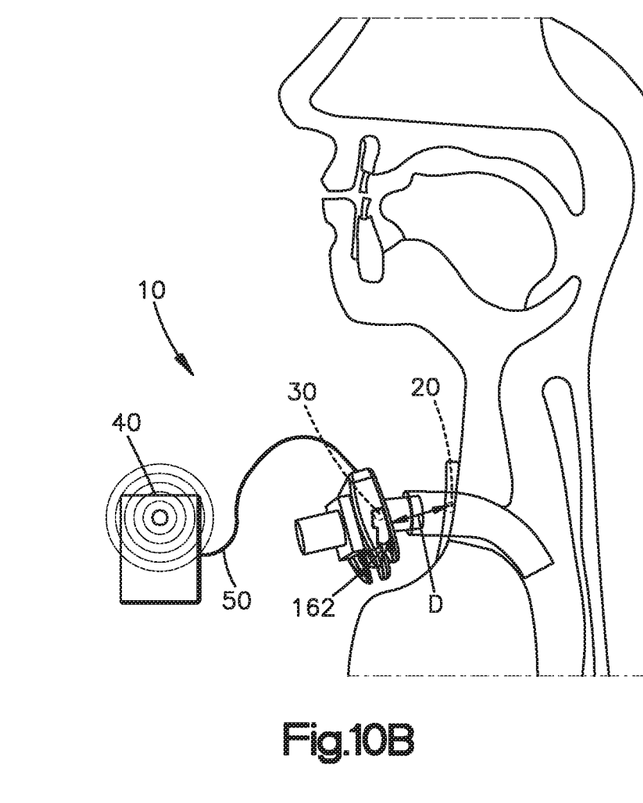
FIG. 10B is a view of the fully assembled alarm assembly illustrated in FIG. 10A, where the alarm circuitry is producing an alert.

With reference to FIGS. 1A-1B, an alarm assembly 10 according to an embodiment of the present disclosure will be described. The alarm assembly 10 can include a wound dressing 20 that is configured to attach to a patient, as will be described further below. The wound dressing 20 can comprise a variety of materials, including cloth, woven fabric, etc. The alarm assembly 10 can further include a sensor holder 30 that is configured to attach to a medical tube T (FIGS. 10A-10B). The medical tube T can be any kind of medical tube T. For example, the medical tube T can be a tracheal tube, such as a tracheostomy tube. In the embodiment illustrated in FIG. 1A, the alarm assembly 10 includes a battery pack 40. However, other embodiments of the alarm assembly 10 will be described below that do not include the battery pack 40. The battery pack 40 can be physically and electrically connected to the sensor holder 30 through a wire 50, which can be configured to transfer power from the battery pack 40 to the sensor holder 30, and signals to the battery pack 40 from the sensor holder 30. The battery pack 40 may include an external indicator, such as an LED light 46, that indicates whether the battery pack 40 is powered on. The battery pack 40 may also include a switch 47 that allows a caregiver or patient turn the battery pack 40 on and off. The battery pack 40 may be powered using batteries (not shown) contained within the battery pack 40, where the batteries may be rechargeable or non-rechargeable.

FIG. 1B depicts the alarm assembly 10 of FIG. 1A attached to a patient. In this figure, the wound dressing 20 is attached to the patient at a location on the patient's skin such that the wound dressing 20 substantially surrounds a stoma S through which the medical tube T, in this case a trach tube, enters the patient. The sensor holder 30 is attached to the medical tube T such that when the medical tube T is fully inserted through the stoma S into the patient, the sensor holder 30 is immediately adjacent to the wound dressing 20. This corresponds to a position where the alarm circuitry 45 is not producing an alert, as will be discussed later. FIG. 1B shows the sensor holder 30 attached to the battery pack 40, which contains the alarm circuitry 45, through a wire 50.

Continuing to FIGS. 2A-2E, a sensor holder 30 of one embodiment of the present disclosure will be described. The sensor holder 30 can define a body 100, which can be formed from a composite, metal, or any other material as desired. The sensor holder 30 can also be produced using any manufacturing method as desired. For example, the sensor holder 30 can be cast, machined, molded, formed, etc. The body 100 of the sensor holder 30 defines an outer surface 101, which can include an upper surface 101a, a lower surface 101b spaced from the upper surface 101a along the transverse direction 14, a rear surface 101c, a left side surface 101d, and a right side surface 101e spaced from the left side surface 101d along the lateral direction 13.

Figure 2A:
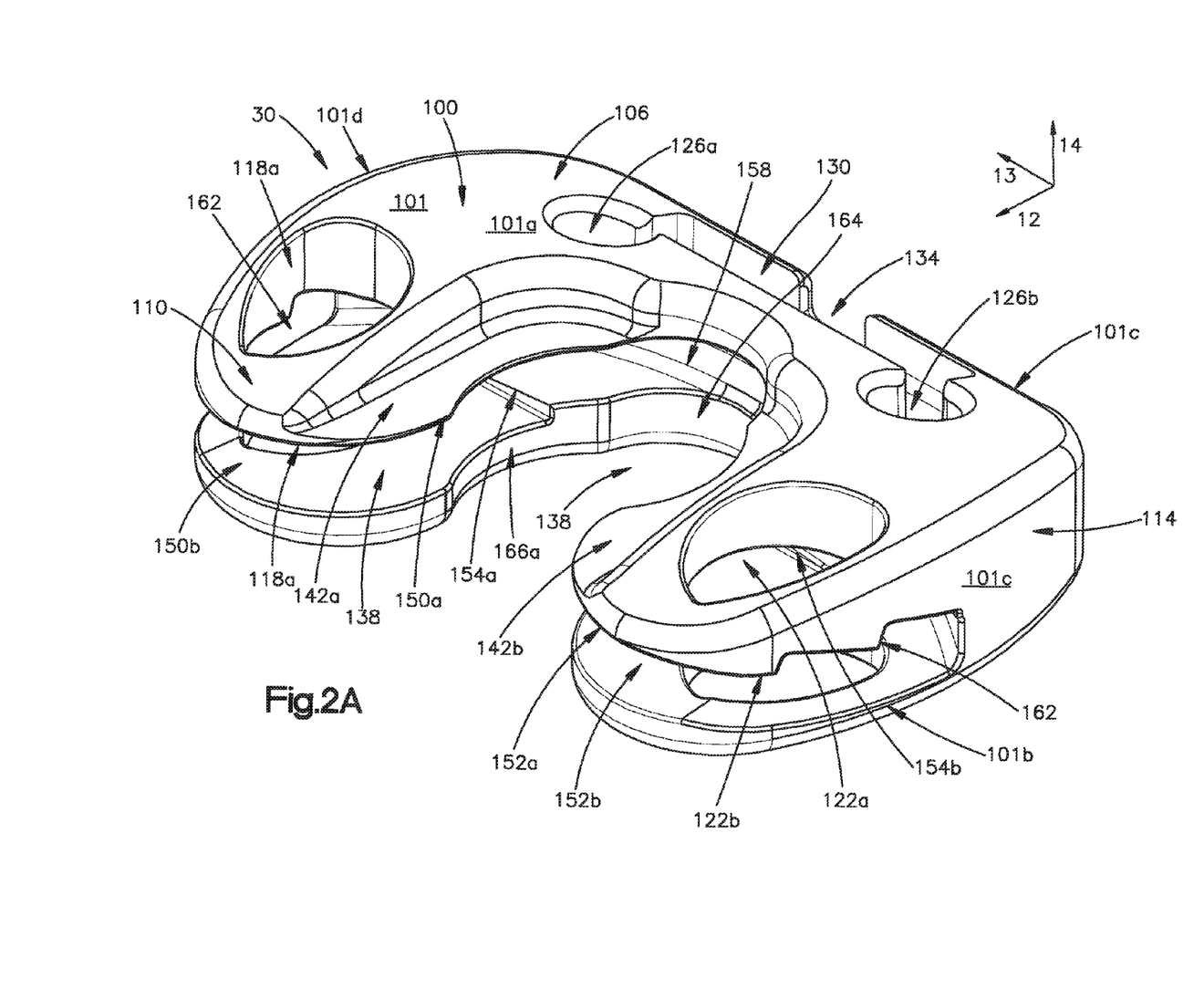
FIG. 2A is a perspective view of a sensor holder according to an embodiment of the present disclosure.

The sensor holder 30 can include a left recess 126a and a right recess 126b. Though FIG. 2A shows the left and right recesses 126a and 126b as spaced apart along the lateral direction 13, the left and right recesses 126a and 126b can be spaced apart along any direction as desired. Additionally, the sensor holder 30 can only include one of the left and right recesses 126a and 126b, additional recesses, or none of the left and right recesses 126a and 126b. Though the left and right recesses 126a and 126b are depicted as being substantially cylindrical, the left and right recesses can take any shape as desired. In one embodiment, the left and right recesses 126a and 126b can extend into the body 100 from the upper surface 101a. The left and right recesses 126a and 126b can each be configured to receive a sensor, such as sensor 60 (described further below).

The sensor holder 30 can also include a central recess 130 that extends into the body 100 of the sensor holder 30. The central recess 130 can be configured to connect the left and right recesses 126a and 126, though the central recess 130 can be open to only one or none of the left and right recesses 126a and 126b. The central recess 130 can be configured to house wires (not shown) or other connecting devices that can connect the sensors received within the left and right recesses 126a and 126b to an external device, such as the battery pack 40. The wires can extend from the central recess 130 through a rear gap 134, which can extend through the rear surface 101c of the sensor holder 30. However, the rear gap 134 can extend through any of the surfaces of the sensor holder 30 as desired. Alternatively, the central recess 130 can house a wireless transmission means (not shown) for transmitting signals to and from the sensors received in the left and right recesses 126a and 126b. Such wireless transmission means can be configured to transmit a variety of signals that include, but are not limited to, electromagnetic, radio, sonic, Wi-Fi, Bluetooth, LTE, or other signals. The left and right recesses 126a and 126b and the central recess 130 can extend from a surface of the sensor holder 30, or can be completely internal to the sensor holder 30 such that none of the left and right recesses 126a and 126b and the central recess 130 are open to the exterior of the sensor holder 30.

In one embodiment of the alarm assembly 10, the sensor holder 30 defines a base 106 that can define the rear surface 101c, and extends from the left side surface 101d to the right side surface 101e. The sensor holder 30 can also define a left tab 110 that extends from the base 106 substantially along the longitudinal direction 12, and a right tab 114 that extends from the base 106 substantially along the longitudinal direction 12. However, the left and right tabs 110 and 114 can extend from the base 106 in any combination of the longitudinal, lateral, and transverse directions 12, 13, and 14 as desired. The left tab 110 can be spaced from the right tab 114 along the lateral direction 13 such that the sensor holder 30 defines a central passage 138 that extends through the body 100 of the sensor holder 30. The central passage 138 can be partially defined by the left tab 110, the right tab 114, and the base 106, and can extend substantially along the transverse direction 14. However, the central passage 138 can also extend along any combination of the longitudinal, lateral, and transverse directions 12, 13, and 14 as desired. The central passage 138 can be configured to receive a portion of a body of a medical tube T, as will be described below.

Figure 2B:
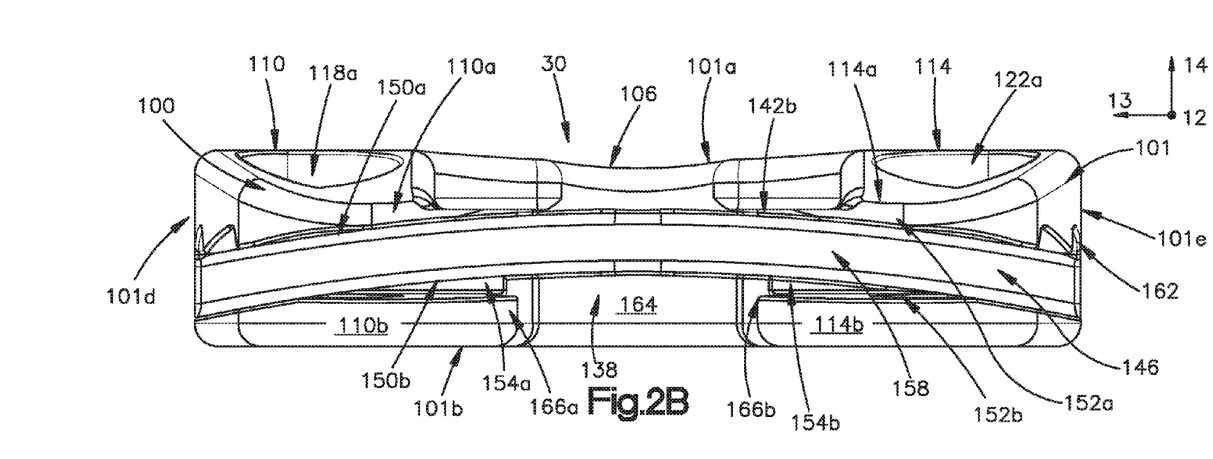
FIG. 2B is a front view of the sensor holder illustrated in FIG. 2A.

With continued reference to FIGS. 2A-2E, the sensor holder 30 can also include a central channel 146 that extends through the body 100 of the sensor holder 30. The central channel 146 can extend from the left tab 110 to the right tab 114, and can be disposed between the upper surface 101a and the lower surface 101b of the sensor holder 30. The central channel 146 can extend from the left side surface 101d to the right side surface 101e along the lateral direction 13. However, the central channel 146 can terminate within either of the left or right tabs 110 or 114 along the lateral direction 13 as desired. In FIG. 2B, the central channel 146 is depicted as curving towards the upper surface 101a. In other embodiments, the central channel 146 can be depicted as curving towards the lower surface 101b, or can extend along a direction that is substantially parallel to the lateral direction 13. The central channel 146 can also extend from the front of the sensor holder 30 to a point within the body 100 of the sensor holder 30, such that the central channel 146 terminates at a point along the longitudinal direction 12 that is spaced from the rear surface 101c. However, a portion of the central channel 146 can extend to the rear surface 101c. The central channel 146 can be configured to receive portions of a medical tube T, as will be described below.

The central channel 146 can extend through the body 100 of the sensor holder 30 such that each of the left and right tabs 110 and 114 is divided into upper and lower portions. For example, the central channel 146 can extend through the left tab 110 between the upper surface 101a and the lower surface 101b such that the left tab 110 is divided into an upper section 110a and a lower section 110b. The lower section 110b of the left tab 110 can be spaced from the upper section 110a of the left tab 110 along the transverse direction 14. Likewise, the central channel 146 can extend through the right tab 114 between the upper surface 101a and the lower surface 101b such that the right tab 114 is divided into an upper section 114a and a lower section 114b. The lower section 114b of the right tab 114 can be spaced from the upper section 114a of the right tab 114 along the transverse direction 14. The lower section 110b of the left tab 110 can be aligned along the transverse direction 14 with the lower section 114b of the right tab 114, and the upper section 110a of the left tab 110 can be aligned along the transverse direction 14 with the upper section 114a of the right tab 114. However, the upper sections 110a and 114a and the lower sections 110b and 114b can be offset from each other along the transverse direction 14 as desired.

Figure 2C:
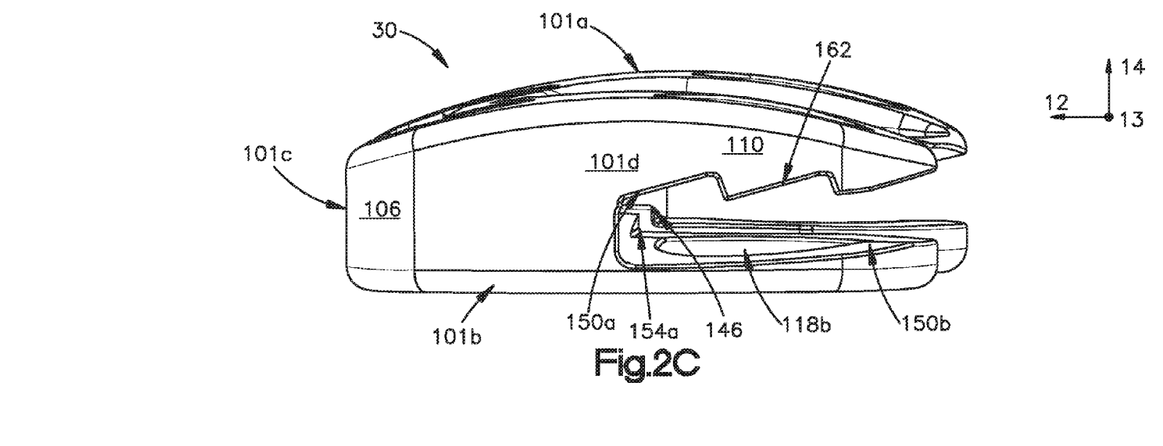
FIG. 2C is a side view of the sensor holder illustrated in FIG. 2A.

The upper section 110a of the left tab 110 can define a first inner surface 150a that is spaced from the upper surface 101a along the transverse direction 14 and partially defines the central channel 146. Likewise, the lower section 110b of the left tab 110 can define a second inner surface 150b that is spaced from the lower surface 101b along the transverse direction 14 and partially defines the central channel 146. The first and second inner surfaces 150a and 150b can be spaced apart along the transverse direction 14, and can be configured to face each other. Similarly, the upper section 114a of the right tab 114 can define a third inner surface 152a that is spaced from the upper surface 101a along the transverse direction 14 and partially defines the central channel 146. The lower section 114b of the right tab 114 can define a fourth inner surface 152b that is spaced from the lower surface 101b along the transverse direction 14 and can partially define the central channel 146. The third and fourth inner surfaces 152a and 152b can be spaced apart along the transverse direction 14, and can be configured to face each other. As shown in FIGS. 2A-2C, the first and third surfaces 150a and 152a can define engagement devices 162 that extend from the first and third inner surfaces 150a and 152a towards the second and fourth inner surface 150b and 152b, respectively. Though the engagement devices 162 shown in FIGS. 2A-2C are depicted as teeth, the engagement devices 162 can take other forms as desired, such as spikes or ridges. Additionally, the engagement devices 162 are not restricted to the first and third inner surfaces 150a and 152a. The engagement devices 162 can extend from any combination of the first, second, third, and fourth inner surfaces 150a, 150b, 152a, and 152b as desired. Alternatively, the sensor holder 30 may not include any engagement devices 162. The engagement devices 162 can be configured to engage part of a medical tube, as will be discussed further below. Further, the second inner surface 150b can include a left inner ledge 154a that extends substantially in the transverse 14 direction. Also, the fourth inner surface 152b can include a right inner ledge 154b that extends substantially in the transverse direction 14. The left and right inner ledges 154a and 154b can divide the second and fourth inner surfaces 150b and 152b into different sections that are spaced apart along the transverse direction 14.

Figure 2D:
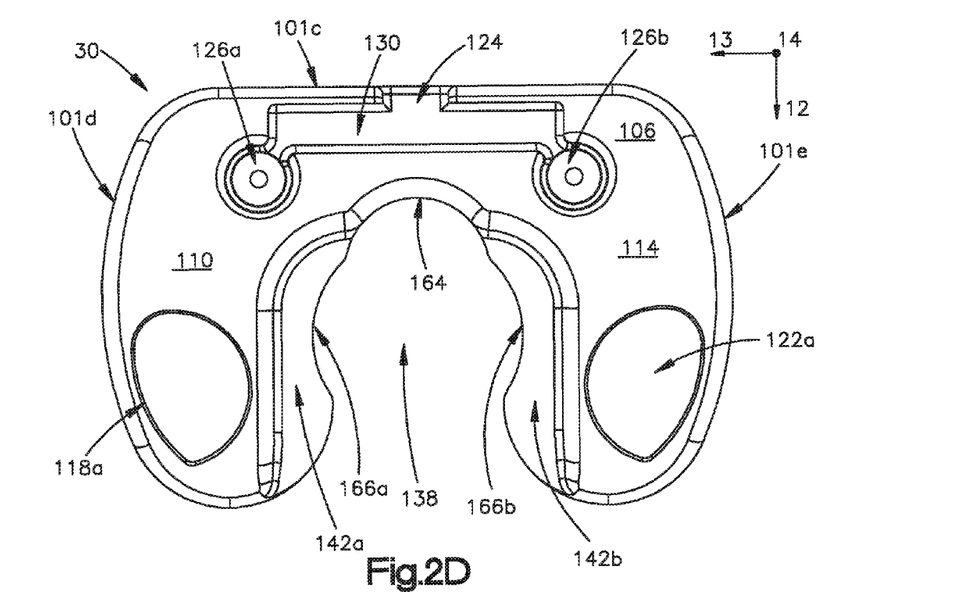
FIG. 2D is a top plan view of the sensor holder illustrated in FIG. 2A.
Figure 2E:
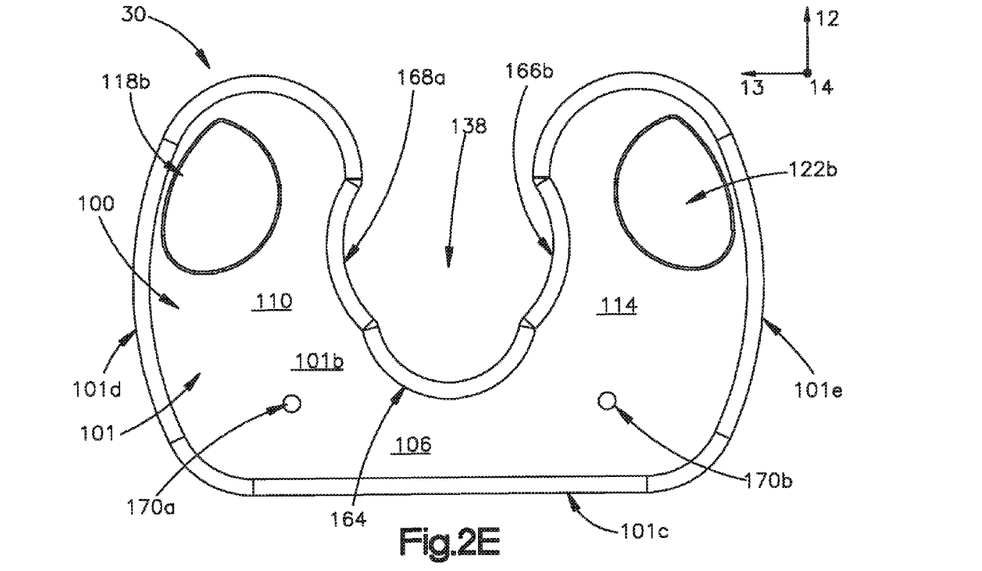
FIG. 2E is a bottom view of the sensor holder illustrated in FIG. 2A.

With reference to FIGS. 2D and 2E, the left and right tabs 110 and 114 can also include passages that extend from the outer surface 101 to the central channel 146. For example, the upper section 110a of the left tab 110 can define a left upper tab passage 118a that extends from the upper surface 101a to the first inner surface 150a. Further, the lower section 110b of the left tab 110 can define a left lower tab passage 118b that extends from the lower surface 101b to the second inner surface 150b. Similarly, the upper section 114a of the right tab 114 can define a right upper tab passage 122a that extends from the upper surface 101a to the third inner surface 152a, and the lower section 114b of the right tab 114 can define a right lower tab passage 122b that extends from the lower surface 101b to the fourth inner surface 152b. Each of the left upper tab passage 118a, left lower tab passage 118b, right upper tab passage 122a, and right lower passage 122b can be in communication with the central channel 146. Additionally, the left upper tab passage 118a and the left lower tab passage 118b can be aligned along the longitudinal and lateral directions 12 and 13. Likewise, the right upper tab passage 122a and the right lower tab passage 122b can be aligned along the longitudinal and lateral directions 12 and 13. Alternatively, the left upper tab passage 118a and the left lower tab passage 118b may not be aligned, and the right upper tab passage 122a and the right lower tab passage 122b may not be aligned along the longitudinal and lateral directions 12 and 13.

Referring to FIGS. 2A, 2B, and 2D, a portion of the upper surface 101a near the central passage 138 can define a left ledge 142a and a right ledge 142b. The left and right ledges 142a and 142b can be offset from the rest of the upper surface 101a along the transverse direction. The left ledge 142a can be partially defined by the left tab 110, or a combination of the left tab 110 and the base 106. Similarly, the right ledge 142b can be partially defined by the right tab 114, or a combination of the right tab 114 and the base 106. The sensor holder 30 can include both the left and right ledges 142a and 142b or only one of the left and right ledges 142a and 142b. Alternatively, the sensor holder 30 can include neither of the left and right ledges 142a and 142b, such that the upper surface 101a is substantially planar.

Turning to FIGS. 2A, 2B, and 2E, the central channel 146 can be partially defined by a rear inner surface 158 that extends between the upper and lower sections 110a and 110b of the left tab 110, and between the upper and lower sections 114a and 114b of the right tab 114. The rear inner surface 158 can extend from the first inner surface 150a to the second inner surface 150b. Additionally, the rear inner surface 158 can extend from the third inner surface 152a to the fourth inner surface 152b. The rear inner surface 158 can extend from the left side surface 101d to the right side surface 101e. Alternatively, the rear inner surface 158 can terminate at its left side at a location disposed inward of the left side surface 101d, and/or at its right side at a location disposed inward of the right side surface 101e. The rear inner surface 158 can extend substantially parallel to the transverse direction 14. In other embodiments, the rear inner surface 158 can include directional components along the longitudinal and lateral directions 12 and 13 as desired.

The central passage 138 can also be defined by a left passage surface 166a that is defined by the lower section 110b of the left tab 110, and a right passage surface 166b that is defined by the lower section 114b of the right tab 114. Each of the left and right passage surfaces 166a and 166b can be substantially curved, such that the sensor holder 30 defines an interference fit with a medical tube T, as will be described further below. The left passage surface 166a can extend from the lower surface 101b to the second inner surface 150b, and the right passage surface 166b can extend from the lower surface 101b to the fourth inner surface 152b. The sensor holder 30 can further define a rear passage surface 164 that extends between the left and right passage surfaces 166a and 166b. The rear passage surface 164 can be curved, straight, or take any shape as desired. The rear passage surface 164 can extend from the lower surface 101b to the rear inner surface 158.

Turning to FIG. 2E, the sensor holder 30 can define a left rear passage 170a, and a right rear passage 170b. Each of the left and right rear passages 170a and 170b can extend from the lower surface 101b of the sensor holder to an interior location in the body 100 of the sensor holder 30. For example, the left rear passage 170a can extend from the lower surface 101b to the left recess 126a, and the right rear passage 170b can extend from the lower surface 101b to the right recess 126b. However, the left and right rear passages 170a and 170b can extend from the lower surface 101b to any location within the body 100 of the sensor holder 30 as desired.

Figures 3, 4A, 4B:
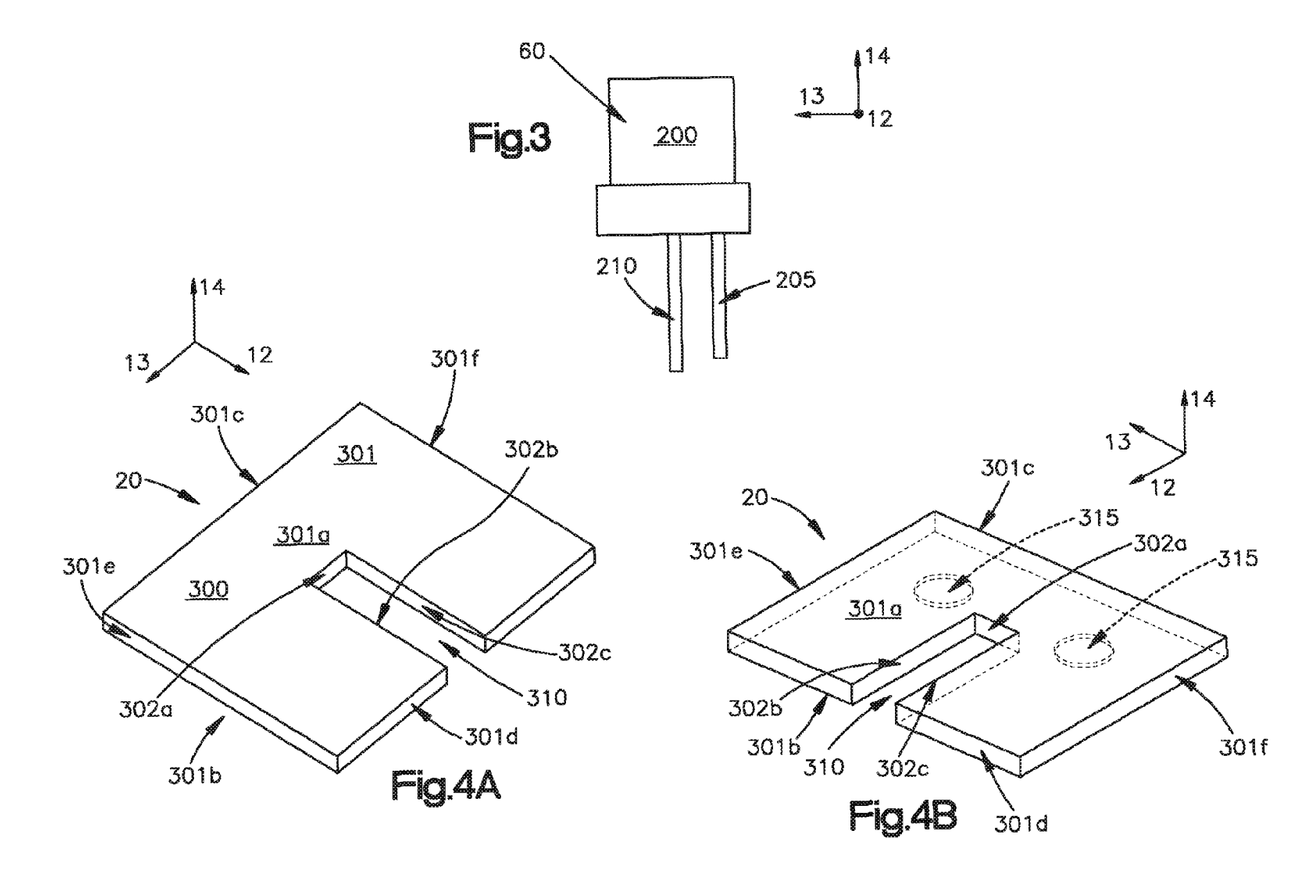
FIG. 3 is a front view of a sensor according to an embodiment of the present disclosure.
FIG. 4A is a perspective view of a wound dressing according to an embodiment of the present disclosure.
FIG. 4B is an alternative perspective view of the wound dressing illustrated in FIG. 4A.

Now referring to FIG. 3, the alarm assembly 10 further includes a sensor 60. The sensor 60 can include a body 200 and pins 205 and 210 that extend from the body 200 in the transverse direction 14. In one embodiment, the sensor 60 is a Reed switch. However, other embodiments of sensor 60 are contemplated by this disclosure, such as coils, circuits, Reed sensors, Hall Effect sensors, magnetic actuators, reed relays, etc. Such sensors are commonly known in the art, and further disclosure of their structure will not be elaborated on here. The sensor 60 can further include a communication means for transmitting information to alarm circuitry 45, which will be described further below. The sensor 60 can be received in the left recess 126a and/or the right recess 126b of the sensor holder 30.

Figure 4C:
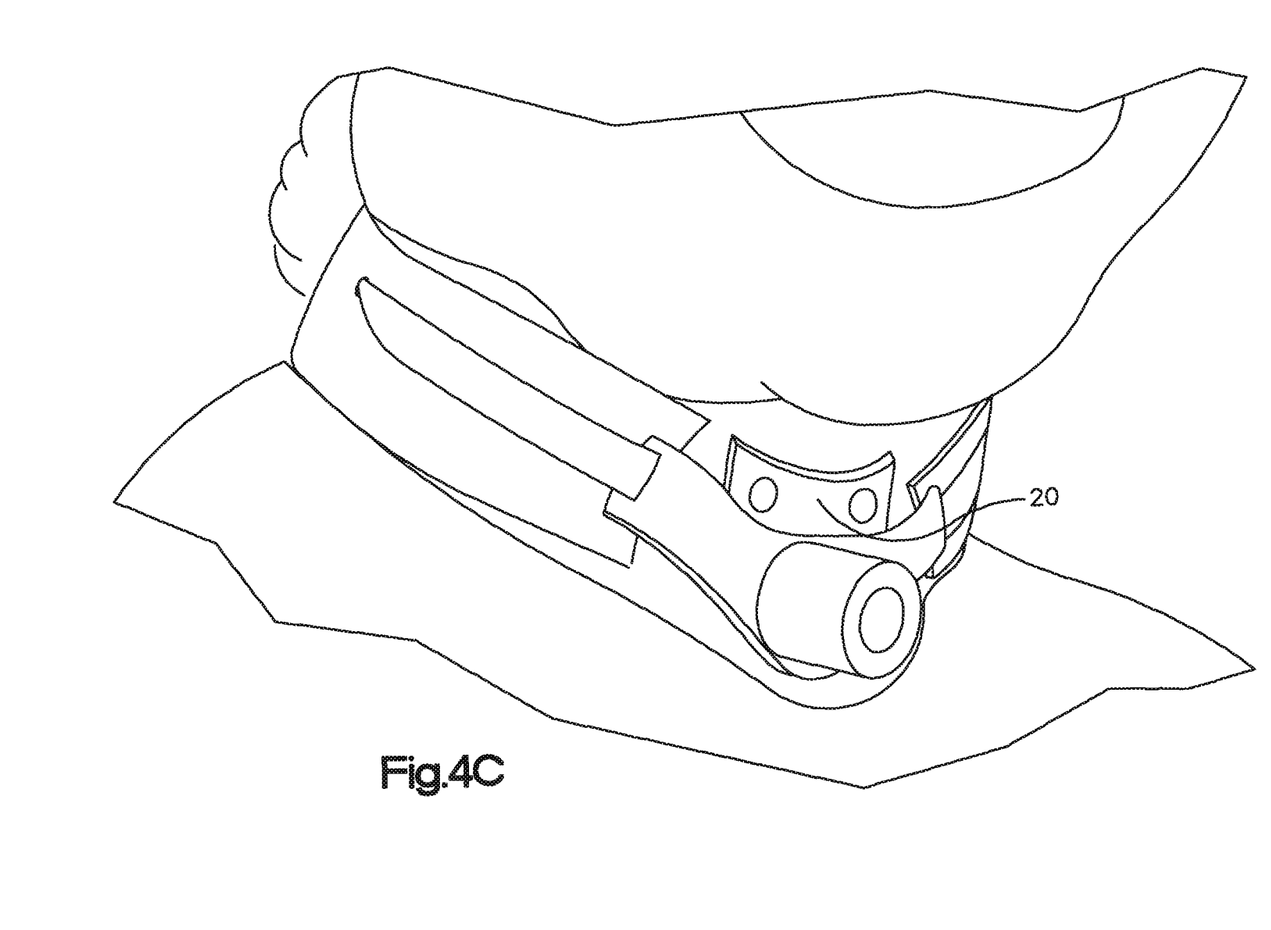
FIG. 4C is a view of the wound dressing illustrated in FIG. 4A attached to a patient.

Turning to FIGS. 4A-4C, an embodiment of the wound dressing 20 will be described. The wound dressing 20 can define a body 300 that includes an outer surface 301. The outer surface 301 can include an upper surface 301a, a lower surface 301b opposite the upper surface 301a along the transverse direction 14, a rear surface 301c, a front surface 301d opposite the rear surface 301c along the longitudinal direction 12, a left side surface 301e, and a right side surface 301f opposite the left side surface 301e along the lateral direction 13. The wound dressing 20, as depicted in FIGS. 4A and 4B, can be substantially rectangular. The wound dressing 20 can be configured to be directly attached to a patient's body. For example, the lower surface 301b can include an adhesive layer that allows the wound dressing 20 to be releasably attached to the skin of the patient. Alternatively, the wound dressing 20 can be attached to a patient through medical tape, liquid adhesive, or other means as desired. The wound dressing 20 can include a central channel 310 that extends from the front surface 301d into the body 300 of the wound dressing 20. However, the central channel 310 can extend from any surface of the wound dressing 20 as desired. The central channel 310 can be defined by a rear inner surface 302a, a left inner surface 302b, and a right inner surface 302c. The rear inner surface 302a, a left inner surface 302b, and a right inner surface 302c can extend from the upper surface 301a to the lower surface 301b. The left inner surface 302b and the right inner surface 302c can extend from the rear inner surface 302a to the front surface 301d, and the rear inner surface 302a can extend from the left inner surface 302b to the right inner surface 302c. The wound dressing 20 can be positioned on a patient such that the central channel 310 aligns with a passage, such as a stoma S (FIGS. 10A-10B), into the patient's body, as will be discussed further below. Accordingly, the central channel 310 can be configured such that a medical tube T extends from the passage through the central channel 310. Also, in reference to FIG. 4B, the wound dressing 20 can include actuators 315, which can be magnets. In one embodiment, the actuators 315 are disposed within the body 300 of the wound dressing 20. Alternatively, the actuators 315 can be disposed on any portion of the outer surface 301 of the wound dressing 20 as desired. The wound dressing 20 can be comprised of any material as desired, such as foam, composite, woven fabric, nonwoven fabric, etc. In one embodiment, the wound dressing 20 is comprised of a material that allows it to be easily disposable. FIG. 4C shows the wound dressing 20 attached to a patient between a portion of a medical tube T and the patient.

Figure 5:
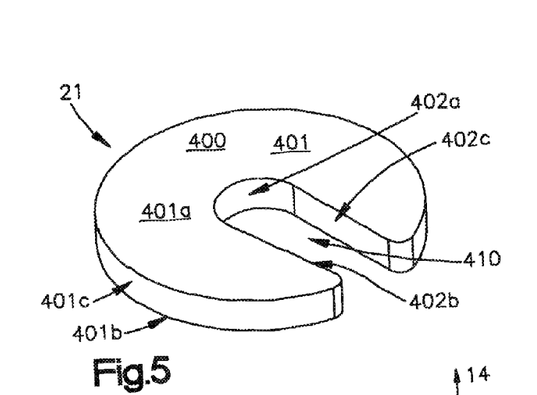
FIG. 5 is a perspective view of a wound dressing according to an alternative embodiment of the present disclosure.

With reference to FIG. 5, another embodiment of a wound dressing 21 will be discussed. The wound dressing 21 can define a body 400 that includes an outer surface 401. The outer surface 401 can include an upper surface 401a, a lower surface 401b opposite the upper surface 401a along the transverse direction 14, and a side surface 401c that extends from the upper surface 401a to the lower surface 401b. The wound dressing 21 of this embodiment is depicted as substantially circular. The wound dressing 21 can include a central channel 410 that extends from the side surface 401c into the body 400 of the wound dressing 21. The central channel 410 can be defined by a rear inner surface 402a, a left inner surface 402b, and a right inner surface 402c. The rear, left, and right inner surface 402a, 402b, and 402c can extend from the upper surface 401a to the lower surface 401b. The left inner surface 402b and the right inner surface 402c can extend from the rear inner surface 402a to the side surface 401c, and the rear inner surface 402a can extend from the left inner surface 402b to the right inner surface 402c. As opposed to the rear inner surface 302a of the wound dressing 20, the rear inner surface 402a of the wound dressing 21 is substantially curved. However, the rear inner surface 402a can take any shape as desired. The wound dressing 21 can have a similar functionality and can be comprised of similar materials as the wound dressing 20. As such, these features will not be repeated here. Also, the wound dressing 21 can include actuators 315, as discussed above with reference to FIGS. 4A and 4B.

Figure 6:
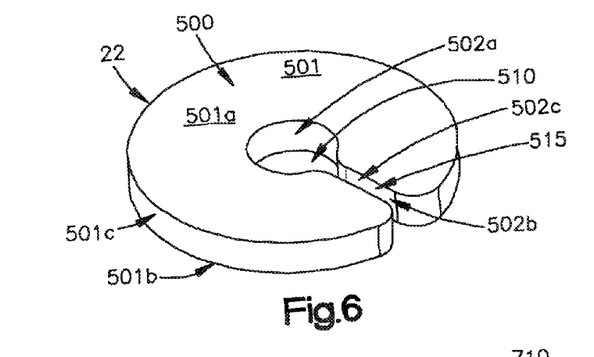
FIG. 6 is a perspective view of a wound dressing according to an alternative embodiment of the present disclosure.

With reference to FIG. 6, another embodiment of a wound dressing 22 will be discussed. The wound dressing 22 can define a body 500 that includes an outer surface 501. The outer surface 501 can include an upper surface 501a, a lower surface 501b opposite the upper surface 501a along the transverse direction 14, and a side surface 501c that extends from the upper surface 501a to the lower surface 501b. The wound dressing 22, as depicted in FIG. 6, can be substantially circular. The wound dressing 22 can include a central passage 515 that extends from the side surface 501c to a central channel 510 that is defined in the body 500 of the wound dressing 22. The central channel 510 can be defined by a rear inner surface 502a, and can extend from the upper surface 501a to the lower surface 501b. The central passage 515 can be defined by a left inner surface 502b and a right inner surface 502c that each extend from the side surface 501c to the rear inner surface 501a. The central channel 510 and the central passage 515 can each define a maximum diameter, where the maximum diameter of the central channel 510 is larger than the maximum diameter of the central passage 515. The wound dressing 22 can have a similar functionality and can be comprised of similar materials as the wound dressings 20 and 21. As such, these features will not be repeated here. Also, the wound dressing 22 can include actuators 315, as discussed above with reference to FIGS. 4A and 4B.

Figure 7:
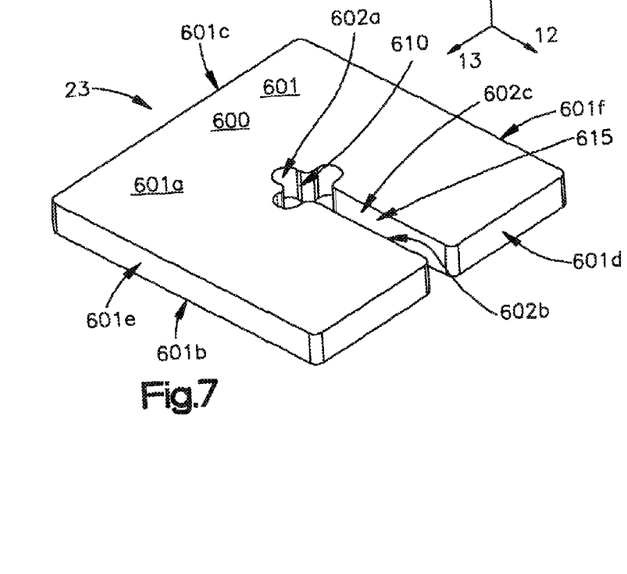
FIG. 7 is a perspective view of a wound dressing according to an alternative embodiment of the present disclosure.

With reference to FIG. 7, another embodiment of a wound dressing 23 will be discussed. The wound dressing 23 can define a body 600 that includes an outer surface 601. The outer surface 601 can include an upper surface 601a, a lower surface 601b opposite the upper surface 601a along the transverse direction 14, a rear surface 601c, a front surface 601d opposite the rear surface 601c along the longitudinal direction 12, a left side surface 601e, and a right side surface 601f opposite the left side surface 601e along the lateral direction 13. The wound dressing 20, as depicted in FIG. 7, can be substantially rectangular. The wound dressing 23 can include a central passage 615 that extends from the side surface 601c to a central channel 610 that is defined in the body 600 of the wound dressing 23. The central channel 610 can be defined by a rear inner surface 602a, and can extend from the upper surface 601a to the lower surface 601b. The central passage 615 can be defined by a left inner surface 602b and a right inner surface 602c that each extend from the side surface 601c to the rear inner surface 601a. In this embodiment, the central channel 610 is substantially clover-shaped. The wound dressing 23 can have a similar functionality and can be comprised of similar materials as the wound dressings 20-22. As such, these features will not be repeated here. Also, the wound dressing 23 can include actuators 315, as discussed above with reference to FIGS. 4A and 4B.

Figure 8:
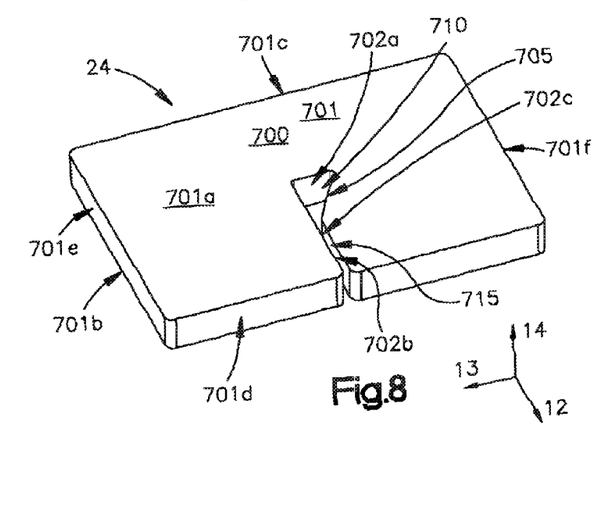
FIG. 8 is a perspective view of a wound dressing according to an alternative embodiment of the present disclosure.

With reference to FIG. 8, another embodiment of a wound dressing 24 will be discussed. The wound dressing 24 can define a body 700 that includes an outer surface 701. The outer surface 701 can include an upper surface 701a, a lower surface 701b opposite the upper surface 701a along the transverse direction 14, a rear surface 701c, a front surface 701d opposite the rear surface 701c along the longitudinal direction 12, a left side surface 701e, and a right side surface 701f opposite the left side surface 701e along the lateral direction 13. The wound dressing 20, as depicted in FIG. 8, can be substantially rectangular. The wound dressing 24 can include a central passage 715 that extends from the front surface 701d to a central channel 710 that is defined in the body 700 of the wound dressing 24. The central channel 710 can be defined by a rear inner surface 702a and a second right inner surface 705, and can extend from the upper surface 701a to the lower surface 701b. The central passage 715 can be defined by a left inner surface 702b and a first right inner surface 702c. The left inner surface 702b can extend from the front surface 701d to the rear inner surface 702a, and the first right inner surface 702c can extend from the front surface 701d to the second right inner surface 705. In this embodiment, the central channel 710 is substantially triangular. The wound dressing 24 can have a similar functionality and can be comprised of similar materials as the wound dressings 20-23. As such, these features will not be repeated here. Also, the wound dressing 24 can include actuators 315, as discussed above with reference to FIGS. 4A and 4B.

Figure 9:
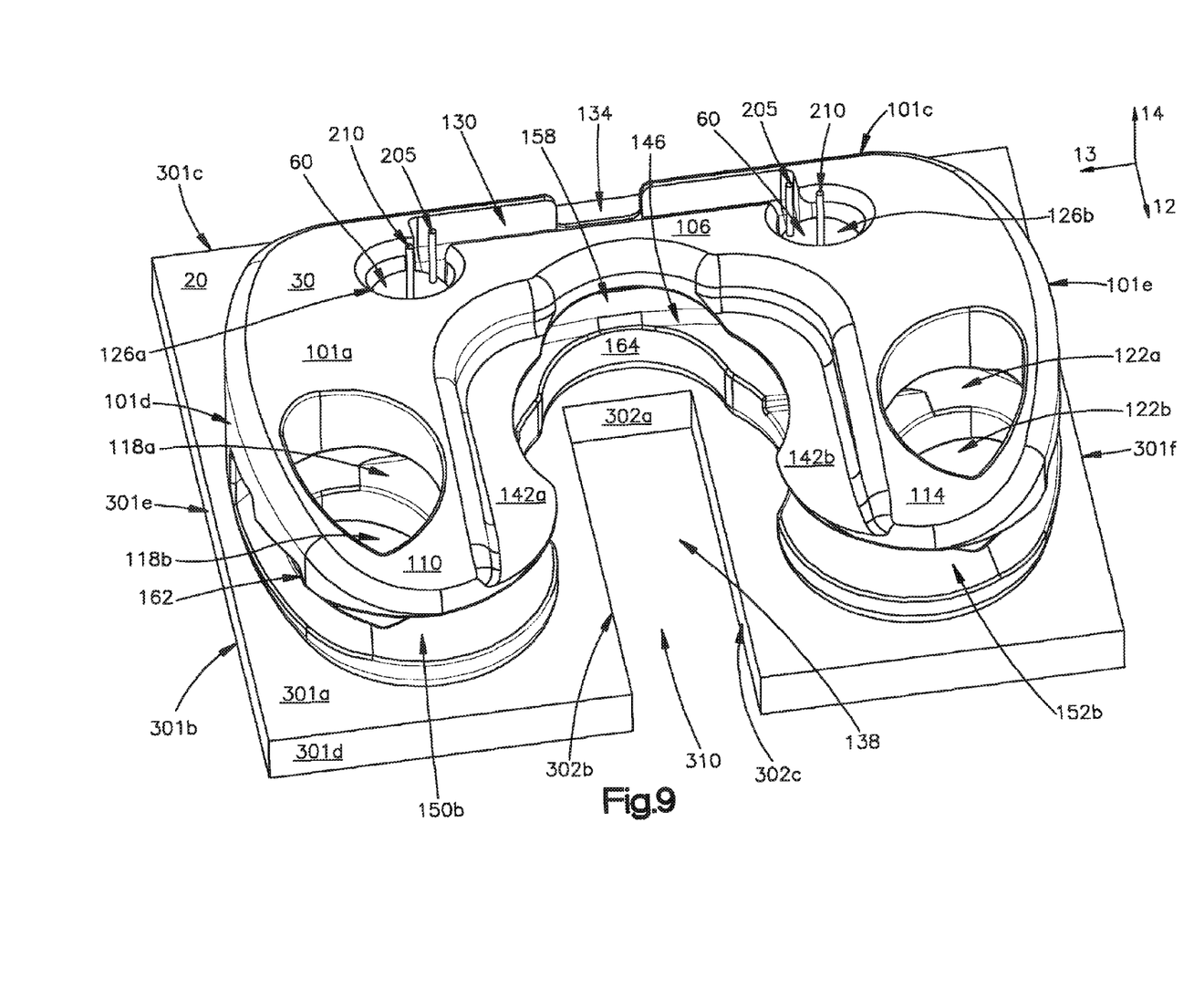
FIG. 9 is a perspective view of a partially assembled alarm assembly according to an embodiment of the present disclosure.

Continuing with FIGS. 9-10B, in operation, a medical professional and/or caregiver can use the alarm assembly 10 to detect when a medical tube T, such as a tracheostomy tube, partially or completely becomes disengaged from a patient. First, as shown in FIG. 10A, the operator can attach the sensor holder 30 to the medical tube T such that the sensor holder 30 is releasably attached to the medical tube T. To do this, a portion of the body of the medical tube T is inserted into the central passage 138 of the sensor holder 30. While the central passage 138 is sized to create an interference fit that keeps the tube T releasably coupled to the sensor holder 30, the sensor holder 30 can also include a central channel 146 that is configured to receive laterally extending tabs of the medical tube T. This interaction between the tabs and central channel 146 aids in keeping the sensor holder 30 attached to the medical tube T. Additionally, the sensor holder 30 can also include engagement devices 162, such as teeth, which can further improve the engagement between the tabs of the medical tube T and the sensor holder 30.

The medical professional and/or caregiver will also attach wound dressing 20 to the skin of the patient, such that the wound dressing 20 substantially surrounds the hole through which the medical tube T enters the patient. In FIG. 10A, this hole is a stoma S. The wound dressing 20 can be attached through an adhesive layer disposed on the wound dressing 20, or through a variety of other means, such as medical tape, separately applied adhesive, etc. After the wound dressing 20 is attached to the patient, the medical tube T is inserted into the patient through the stoma S. Alternatively, the medical tube T may be inserted into the patient through the stoma S before the wound dressing 20 is attached to the patient, as well as before the sensor holder 30 is attached to the medical tube T. When the medical tube T is fully inserted into the patient, the sensor holder 30 and the wound dressing 20 will be disposed adjacent to each other in a first configuration. In this first configuration, the actuators 315 disposed within the wound dressing 20, which can be magnets, cause the switch 60 disposed in the sensor holder 30 to not send a signal to the alarm circuitry 45 contained in the battery pack 40. As such, the alarm circuitry 45 will not produce an alert when the sensor assembly 10 is in the first configuration.

However, as shown in FIG. 10B, the medical tube T can become dislodged from the patient. This can create a variety of health risks for the patient, such as a lack of oxygen. As a result, the patient, medical professional, or other caregiver providing care for the patient will want to know immediately when the medical tube T becomes dislodged in order for corrective action to be quickly taken. When the tube T becomes dislodged as shown in FIG. 10B, the sensor holder 30 becomes physically separated from the wound dressing 20 by a distance D. Once the distance D reaches a predetermined level, the sensor holder 30 will send a signal to the battery pack 40. The signal can be sent from the sensor 60 to the alarm circuitry 45 electrically through the wire 50. However, the sensor 60 can also be configured to send the signal via other means, such as Wi-Fi, Bluetooth, etc. The signal is sent due to the increased distance between the sensor 60 in the sensor holder 30 and the actuators 315 in the wound dressing 20. Upon receiving the signal, the alarm circuitry 45 contained within the battery pack 40 will produce an alert that notifies the caregiver and/or patient that the medical tube T has become dislodged and requires immediate attention. The alert can be auditory, physical, or take a variety of other forms. Optionally, the sensor 60 can include an LED light (not shown) that illuminates when the medical tube T becomes dislodged. Once the patient or caregiver has responded to the alert and placed the medical tube T into its fully inserted position, the sensor 60 will indicate to the alarm circuitry 45 to cease creating the alert. The patient or caregiver can also turn the battery pack 40 off using the switch 47 to stop the alarm while reinserting the medical tube T into the fully inserted position. Though the alarm circuitry 45 is depicted as being contained within battery pack 40, the alarm circuitry 45 can also be contained within other devices. In other embodiments, the alarm circuitry 45 can be contained within a mobile phone, tablet, computer, pager, or similar device. Additionally, the alarm circuitry 45 can comprise any suitable electrical circuitry that is capable of producing an alert.

In another embodiment, it is contemplated that a plethysmograph (not shown) may be used to detect displacement of a medical tube T. Plethysmographs, as well as various methods of plethysmography, are commonly known in the art, and thus will not be described further here.

The present disclosure is described herein using a limited number of embodiments. These specific embodiments are not intended to limit the scope of the disclosure as otherwise described and claimed herein. Modification and variations from the described embodiments exist. More specifically, the examples included are given as a specific illustration of embodiments of the claimed disclosure. It should be understood that the invention is not limited to the specific details set forth in the examples, and that various changes, substitutions, and alterations can be made without departing from the spirit and scope of the invention as defined by the appended claims.

What is claimed:

1. An alarm assembly configured to engage a tube that is capable of extending into a patient, the tube defining a main body, wherein the alarm assembly comprises:
   alarm circuitry;
   a wound dressing configured to releasably attach to the patient, wherein the wound dressing includes at least one actuator; and
   a sensor holder configured to be releasably coupled to the tube, the sensor holder including at least one sensor, wherein when the at least one actuator is configured to actuate the at least one sensor when the at least one sensor moves from a first position to a second position, the second position being further from the at least one actuator than the first position,
   wherein the at least one sensor is configured to transmit a signal to the alarm circuitry when the at least one actuator actuates the at least one sensor, and the alarm circuitry is configured to produce an alert in response to receiving the signal.

2. The alarm assembly of claim 1, wherein the tube is a tracheostomy tube, the at least one actuator is at least one magnet that is configured to produce a magnetic field, and the at least one sensor is at least one magnetic switch.

3. The alarm assembly of claim 1, wherein the sensor holder defines a body that includes an upper surface, a lower surface opposite the upper surface in a transverse direction, a left side surface, and a right side surface opposite the left side surface in a lateral direction that is substantially perpendicular to the transverse direction.

4. The alarm assembly of claim 3, wherein the body defines a central passage that extends through the body of the sensor holder from the upper surface to the lower surface, the central passage being configured to receive a portion of the body of the tube.

5. The alarm assembly of claim 4, wherein the body defines a base, a left tab that extends from the base in a longitudinal direction that is substantially perpendicular to the lateral and transverse directions, and a right tab that extends from the base in the longitudinal direction, wherein the left tab is spaced from the right tab along the lateral direction.

6. The alarm assembly of claim 5, wherein the central passage extends from the left tab to the right tab.

7. The alarm assembly of claim 6, wherein the left tab and the right tab are configured to secure a portion of the tube within the central channel via an interference fit.

8. The alarm assembly of claim 3, wherein the body defines a central channel that extends between the upper surface and the lower surface, the central channel being configured to receive a first portion of the tube that extends from the main body of the tube in a first direction and a second portion of the tube that extends from the main body of the tube in a second direction that is different than the first direction.

9. The alarm assembly of claim 8, wherein the body is configured to secure the first and second portions of the tube within the central channel via an interference fit.

10. The alarm assembly of claim 8, wherein the central channel extends from the left side surface to the right side surface.

11. The alarm assembly of claim 8, wherein the central channel is curved with respect to the lateral direction.

12. The alarm assembly of claim 8, wherein the body defines:
   a base;
   a left tab that extends from the base in a longitudinal direction that is substantially perpendicular to the lateral and transverse directions, the left tab defining a first inner surface and a second inner surface spaced from the first inner surface along the transverse direction, wherein the first and second inner surfaces at least partially define the central channel; and
   a right tab that extends from the base in the longitudinal direction, the right tab defining a third inner surface and a fourth inner surface spaced from the third inner surface along the transverse direction, wherein the third and fourth inner surfaces at least partially define the central channel, wherein the left tab is spaced from the right tab along the lateral direction.

13. The alarm assembly of claim 12, wherein at least one of the first, second, third, and fourth inner surfaces define a plurality of teeth that are configured to contact at least one of the first and second portions of the tube.

14. The alarm assembly of claim 1, wherein the at least one sensor includes a first sensor and a second sensor, and the at least one actuator includes a first actuator and a second actuator, wherein a) the first sensor is aligned with the first actuator along the transverse direction and b) the second sensor is aligned with the second actuator along the transverse direction when 1) the sensor holder is releasably coupled to the tube, and 2) the wound dressing is releasably attached to the patient.

15. The alarm assembly of claim 1, further comprising a wire that extends from the sensor holder to the alarm circuit, wherein the signal is an electrical signal, and the wire is configured to transmit the electrical signal from the sensor to the alarm.

16. The alarm assembly of claim 1, wherein signal is a Bluetooth signal.

17. The alarm assembly of claim 4, wherein the wound dressing defines a dressing upper surface, a dressing lower surface that is opposite the dressing upper surface along the lateral direction, and a dressing central channel that is configured to receive another portion of the body of the tube.

18. A method of detecting a tube dislodging from a patient, the method including the steps of:

attaching a wound dressing to the patient, the wound dressing including at least one actuator;

attaching a sensor holder to the tube, the sensor holder including at least one sensor wherein when the at least one actuator is configured to actuate the at least one sensor when the at least one sensor moves from a first position to a second position, the second position being further from the at least one actuator than the first position;

transmitting a signal from the at least one sensor to an alarm circuitry when the at least one actuator actuates the at least one sensor; and producing an alert via the alarm circuitry when the alarm circuitry receives the signal.

19. The method of claim 18, wherein the tube is a tracheostomy tube, the at least one actuator is at least one magnet that is configured to produce a magnetic field, and the at least one sensor is at least one magnetic switch.

20. A kit comprising:

a tube defining a main body, the tube being capable of extending into a patient;

alarm circuitry;

a wound dressing configured to releasably attach to the patient, wherein the wound dressing includes at least one actuator; and a sensor holder configured to be releasably coupled to the tube, the sensor holder including at least one sensor, wherein when the at least one actuator is configured to actuate the at least one sensor when the at least one sensor moves from a first position to a second position, the second position being further from the at least one actuator than the first position, wherein the at least one sensor is configured to transmit a signal to the alarm circuitry when the at least one actuator actuates the at least one sensor, and the alarm circuitry is configured to produce an alert in response to receiving the signal.

* * * * *